(12) United States Patent
Fong

(10) Patent No.: US 10,932,817 B2
(45) Date of Patent: Mar. 2, 2021

(54) LIGHTING AND OPTICS SURGICAL SYSTEM

(71) Applicant: City of Hope, Duarte, CA (US)

(72) Inventor: Yuman Fong, Duarte, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 16/398,967

(22) Filed: Apr. 30, 2019

(65) Prior Publication Data

US 2019/0328422 A1 Oct. 31, 2019

Related U.S. Application Data

(60) Provisional application No. 62/664,534, filed on Apr. 30, 2018.

(51) Int. Cl.
| | | |
|---|---|---|
| *A61B 17/00* | (2006.01) |
| *A61B 17/34* | (2006.01) |
| *A61B 1/313* | (2006.01) |
| *A61B 90/30* | (2016.01) |
| *A61B 90/00* | (2016.01) |
| *A61B 1/05* | (2006.01) |

(52) U.S. Cl.
CPC ........ *A61B 17/3423* (2013.01); *A61B 1/3132* (2013.01); *A61B 17/00234* (2013.01); *A61B 90/30* (2016.02); *A61B 1/05* (2013.01); *A61B 90/361* (2016.02)

(58) Field of Classification Search
CPC ................ B01D 46/0012; B01D 46/10; B01D 46/0038; B01D 2253/102; B01D 2275/10; A61B 1/0002; A61B 1/00032; A61B 1/3132; A61B 1/00108; A61B 1/07; A61B 1/0684; A61B 1/05; A61B 2017/00734; A61B 17/00234; A61B 17/3423; A61B 17/3421; A61B 90/30; A61B 90/361; A61B 2090/309; A61B 18/00; A61B 2218/008
USPC ....... 600/201–220; 604/35, 45, 264; 95/273, 95/286; 55/385.1, 486, 503, 505, 472
See application file for complete search history.

(56) References Cited

U.S. PATENT DOCUMENTS

| | | | | |
|---|---|---|---|---|
| 6,110,259 A * | 8/2000 | Schultz | .................. | A61B 18/00 55/385.1 |
| 6,544,210 B1 * | 4/2003 | Trudel | ................... | A61B 18/00 604/26 |
| 6,585,731 B1 * | 7/2003 | Rattner | .................. | A61B 50/10 606/34 |
| 9,011,366 B2 * | 4/2015 | Dean | ...................... | A61B 18/00 604/131 |
| 9,943,355 B2 * | 4/2018 | Babini | .................. | A61B 18/04 |
| 2017/0319264 A1 * | 11/2017 | Haupt | ................ | A61B 18/1442 |

(Continued)

*Primary Examiner* — Pedro Philogene
(74) *Attorney, Agent, or Firm* — Mintz Levin Cohn Ferris Glovsky and Popeo, P.C.

(57) ABSTRACT

Lighting and optical devices, systems, and methods are configured for use in laparoscopic surgical procedures. The disclosed devices, systems, and methods advantageously do not require tethers in order to receive power or transmit data, such as camera images, to and from an external device. In addition, the disclosed devices, systems, and methods utilize improved camera mechanisms and reduce costs and improve accessibility with respect to laparoscopic surgical procedures. Furthermore, a smoke evacuator system can be used as part of surgical procedure to evacuate smoke from a surgical setting.

10 Claims, 16 Drawing Sheets

(56) References Cited

U.S. PATENT DOCUMENTS

2018/0036064 A1* 2/2018 Shvetsov ............ A61B 18/1402
2019/0201088 A1* 7/2019 Shelton, IV ........... A61B 34/37

* cited by examiner

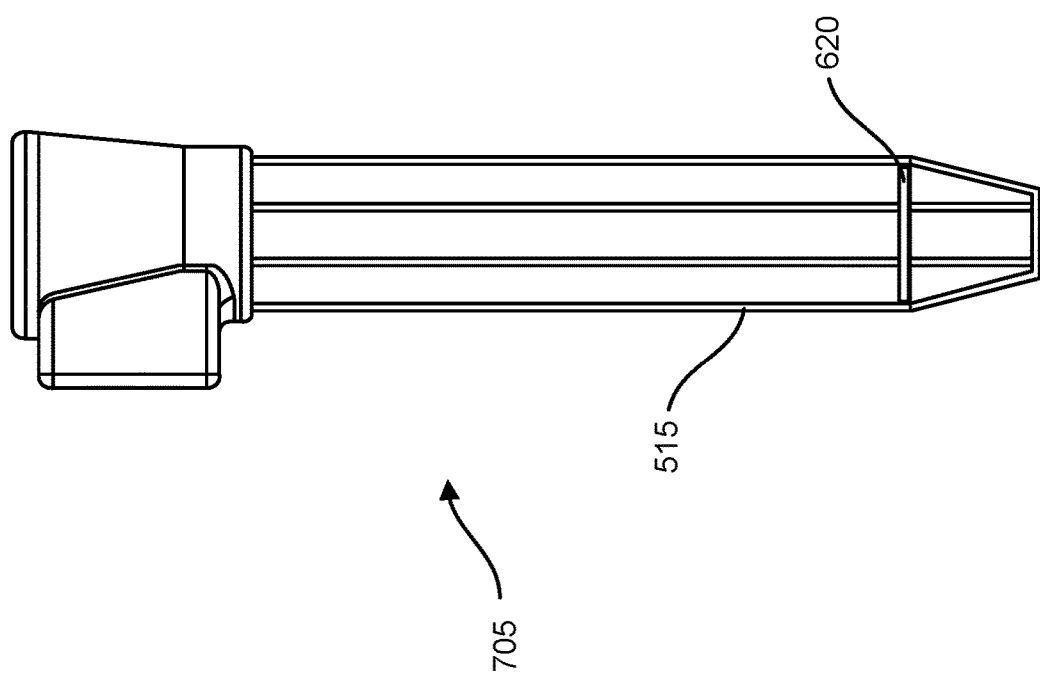

LIGHTING AND OPTICS SURGICAL SYSTEM

CROSS REFERENCE TO PRIORITY APPLICATION

The present application claims priority under 35 U.S.C. § 119 to U.S. Provisional Application Ser. No. 62/664,534 filed Apr. 30, 2018, entitled "Lighting and Optics Surgical System", the disclosure of which is incorporated herein by reference.

BACKGROUND

Laparoscopic surgery is a surgical technique wherein surgical and/or diagnostic procedures are performed through tools that are inserted into a patient through small incisions in the body. The procedure uses an instrument called a laparoscope to view the abdominal organs. The laparoscope is a long, thin tube equipped with a light and a camera. The laparoscope is inserted through an incision in the abdominal wall and is used to illuminate and capture images for viewing.

In a typical laparoscopic procedure, several incisions are made and one or more tubes, cannulas, or trocars are inserted through the incisions. The laparoscope and other instruments are introduced through the tubes to provide access to the inside of the patient. The devices that are inserted into the patient, including the laparoscope, are tethered to a power source or other device, such as a video monitor.

The tethers can be unwieldy and can limit the ability of a surgeon to manipulate the tethered devices. In addition, the light source and the laparoscope is typically a single, hot, and limited range incandescent light that is attached to a lone camera. Such systems are expensive and unwieldy.

In addition, smoke generated during surgical procedures has long been thought to be hazardous to hospital personnel. The dangers of surgical smoke are related to the composition of the plume generated during surgery. Small particulate matter are found in the smoke that are easily inhaled. They deposit in the lungs, circulatory system, and other organs which cause numerous detrimental health problems. The smoke also contains many gaseous compounds known to cause cancer. The type of tissue and the form of cautery have been shown to alter the composition of the surgical smoke. Daily inhaled surgical smoke could be equivalent to smoking dozens of cigarettes. Cancer causing compounds have also been found in unsafe levels in the smoke.

SUMMARY

In view of the foregoing, there is a need for improved lighting and optic systems for laparoscopic surgery. There is also a need for a smoke evacuator system that can be used as part of the surgical procedure, such as a laparoscopic surgery procedure.

Disclosed are lighting and optical devices, systems, and methods for use in laparoscopic surgical procedures. The disclosed devices, systems, and methods advantageously do not require tethers in order to receive power or transmit data, such as camera images, to and from an external device. In addition, the disclosed devices, systems, and methods utilize improved camera mechanisms and reduce costs and improve accessibility with respect to laparoscopic surgical procedures. Also disclosed is a smoke evacuator system that can be used as part of surgical procedure to evacuate smoke from a surgical setting.

In one aspect, there is discloses a laparoscopic surgical system, comprising: elongated body sized and shaped to fit through an incision into a patient's body pursuant to a laparoscopic procedure; a hub on a proximal end of the elongate body; a light source attached to the body, the light source configured to transmit light at least along a longitudinal axis of the elongated body; and a power source directly attached to the elongated body, wherein the power source provide power to the light source; wherein the elongated body does not include any tethers that attach to a remote power source or light source.

In another aspect, there is disclosed a system for evacuating smoke in a surgical setting, comprising a housing; a pump contained in the housing; a power source coupled to the housing; and a tube coupled to the pump, wherein the tube has a portion positionable at a surgical site for drawing smoke from the surgical site as a result of a pressure differential caused by the pump.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

FIG. 7 shows another embodiment of a trocar tool.

DETAILED DESCRIPTION

Disclosed are lighting and optical devices, systems, and methods for use in laparoscopic surgical procedures. The disclosed devices, systems, and methods advantageously do not require tethers in order to receive power or transmit data, such as camera images, to and from an external device. In addition, the disclosed devices, systems, and methods utilize improved camera mechanisms and reduce costs and improve accessibility with respect to laparoscopic surgical procedures.

Also disclosed is a smoke evacuator system that can be used as part of surgical procedure to evacuate smoke from a surgical setting.

Figure 1:
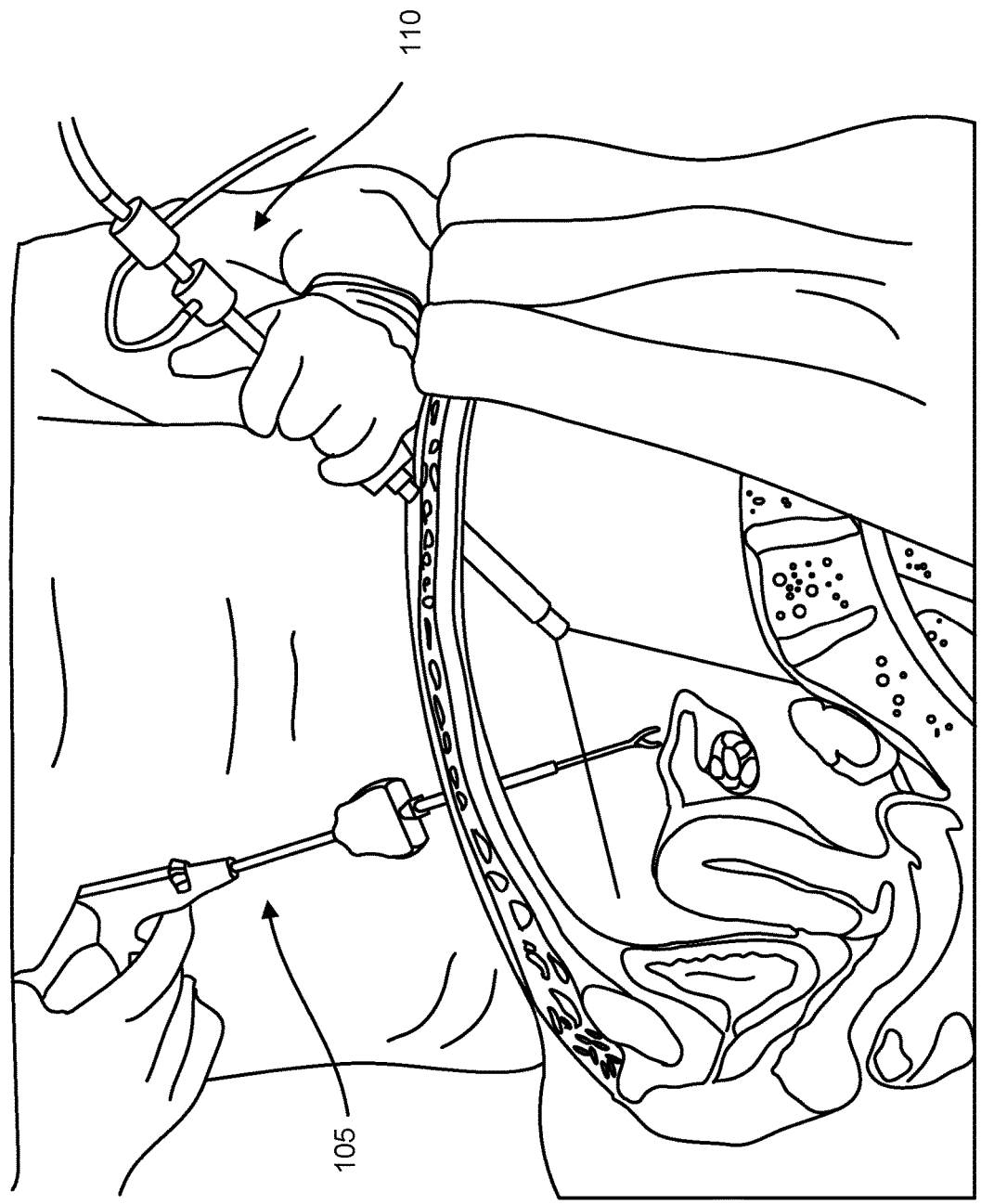
FIG. 1 shows a graphical representation of a laparoscopic surgery procedure.

FIG. 1 shows a graphical representation of a laparoscopic surgical procedure. Pursuant to the procedure, a laparoscopic surgical tool 105 and one or more laparoscopes 110 are inserted through respective incisions made into a belly of the patient. In a conventional system, the laparoscope 110 includes a tether through which power and/or data can be transmitted to and from a light source and camera of the laparoscope 110. Described herein are improved systems that do not require the use of a tether for the laparoscope and that also improve the camera and lighting capability of the laparoscope.

Figure 2:
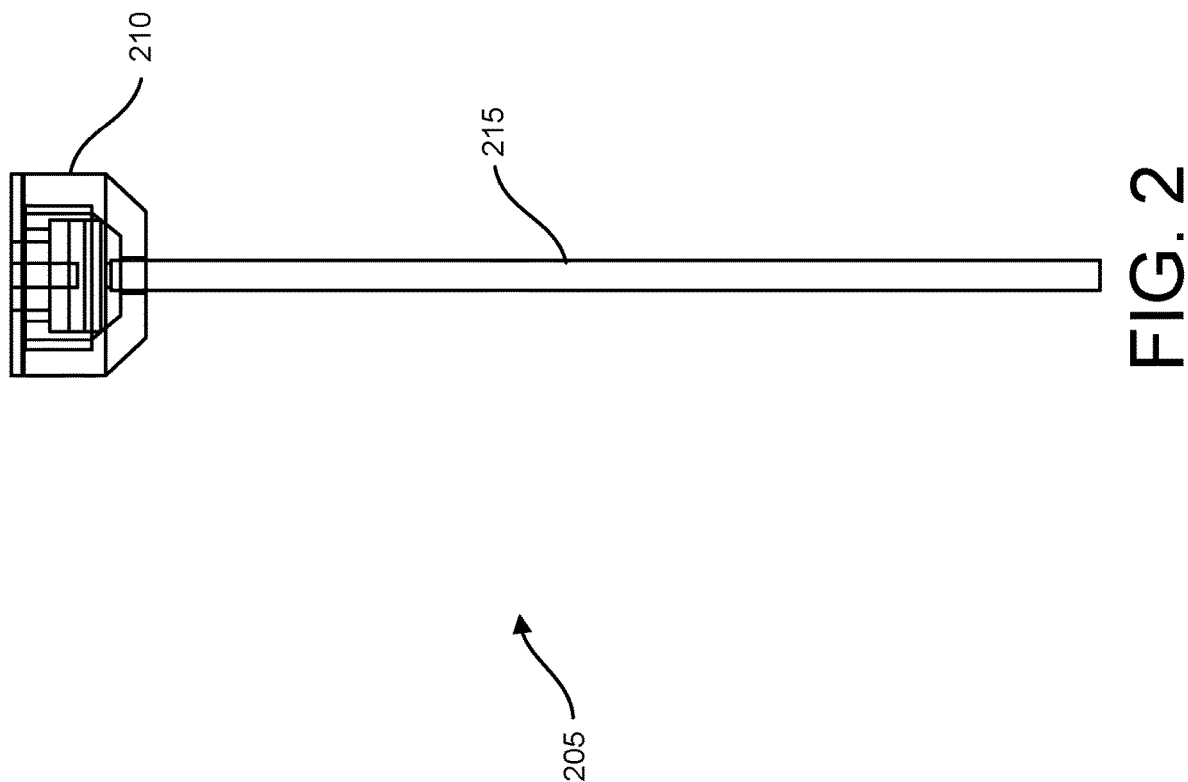
FIG. 2 shows a side view of a light stick for use in laparoscopic surgery.

FIG. 2 shows a side view of a light stick 205 that can be used independently or as part of a laparoscope for providing lighting and/or camera capabilities. The light stick 205 is an elongated body that is sized and shaped to fit through an incision into a patient's body pursuant to a laparoscopic procedure. The light stick 205 includes a proximal hub 210 and an elongated shaft 215 that extends outwardly from the hub 210. The proximal hub 210 can have an elongated diameter (or transverse dimension relative to a long axis) relative to a diameter of the elongated shaft 215. The shaft 215 can be an elongated cylinder with an internal lumen that communicates with an internal portion of the hub 210, wherein the hub 210 can also have an access port or opening that communicates with the lumen. In an example embodiment, the shaft 215 is a cannula. The light stick (or any other of the laparoscopic devices described herein) do not include and/or do not require a tether in order to receive power or transmit data.

Figure 3:
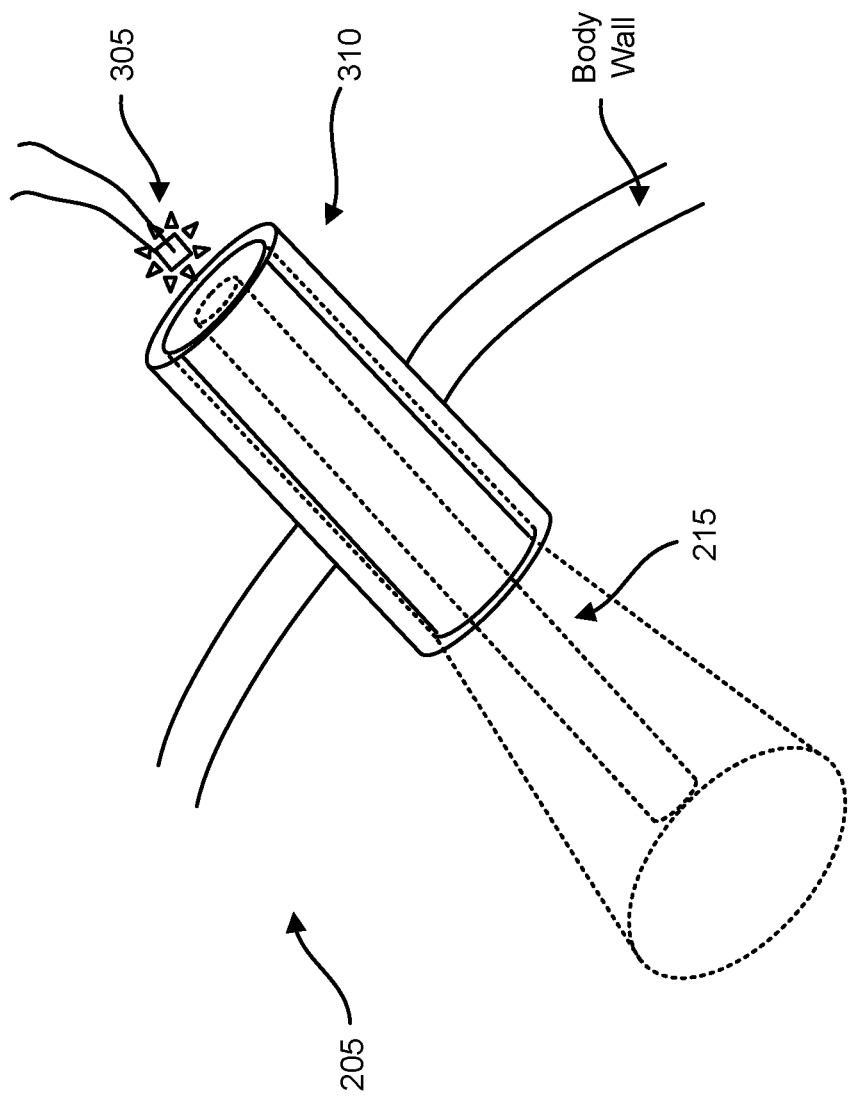
FIG. 3 shows a schematic representation of the light stick of FIG. 2.

In an embodiment, the light stick 205 is dedicated solely for providing lighting capabilities pursuant to a laparoscopic procedure. For example, as shown in FIG. 3, the shaft 215 of the light stick 205 can be a cylindrical body that is made of a material that transmits light. For example, the material can be acrylic. A trocar 310 can be positioned through an incision in the body wall and can provide a passageway for the light stick 205 to be inserted into the body. The trocar can be a cylindrical body with a lumen sized to receive the light stick 215 therethrough. A light source, such as an LED 305 is positioned in the hub 210 of the light stick such a in a proximal region or proximal end of the light stick.

Thus, in this embodiment, the light source is positioned at the proximal end, or top, of the light stick 205 such that when illuminated light is transmitted through the shaft 215 toward the distal end of the shaft 215. The LED 305 can be coupled to a printed circuit board, such as a single printed circuit board position at or near the hub 210.

Figure 4:
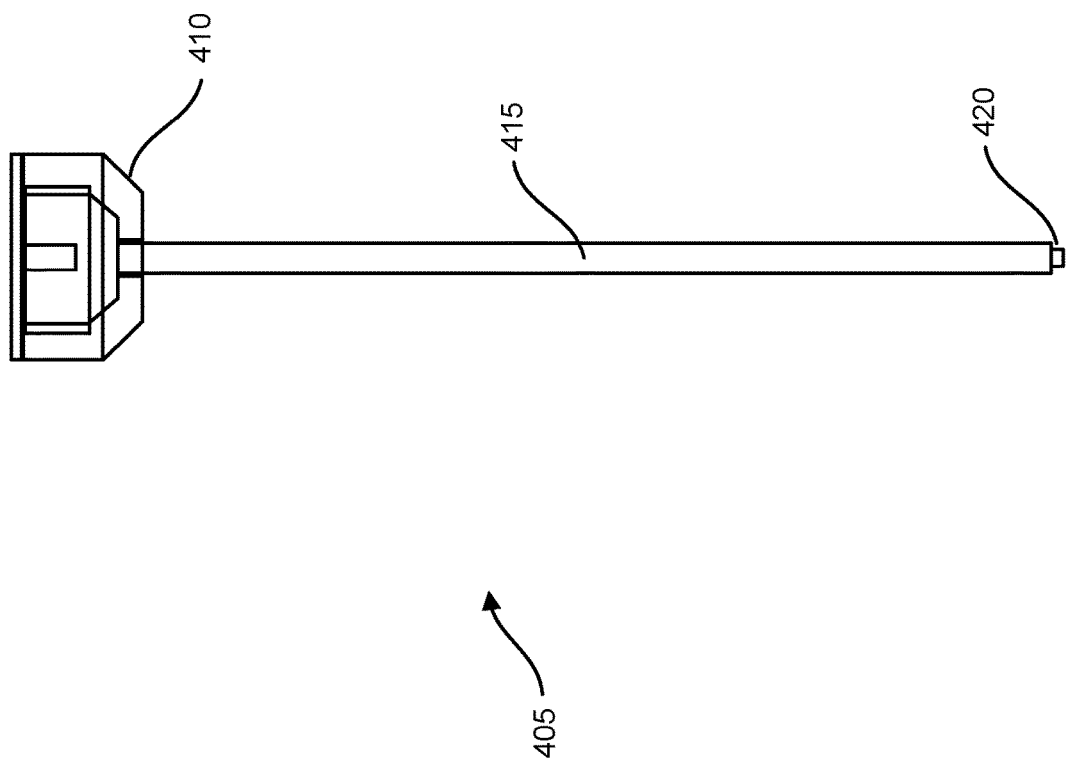
FIG. 4 shows a side view of a cannula tool for use in laparoscopic surgery.

FIG. 4 shows an embodiment of a cannula tool 405 that can be used independently or as part of a laparoscope system for providing lighting and/or camera capabilities. The cannula tool 405 includes a proximal hub 410, an elongated shaft 415 that extend outwardly from the hub 410, and a light source 420 located at a distal end, or bottom, of the elongated shaft 415. The light source 420 can also be at a distal region rather than a distal end of the elongated shaft 415 In an embodiment, the light source 420 is an LED although it should be appreciated that the type of light source can vary.

Figure 6:
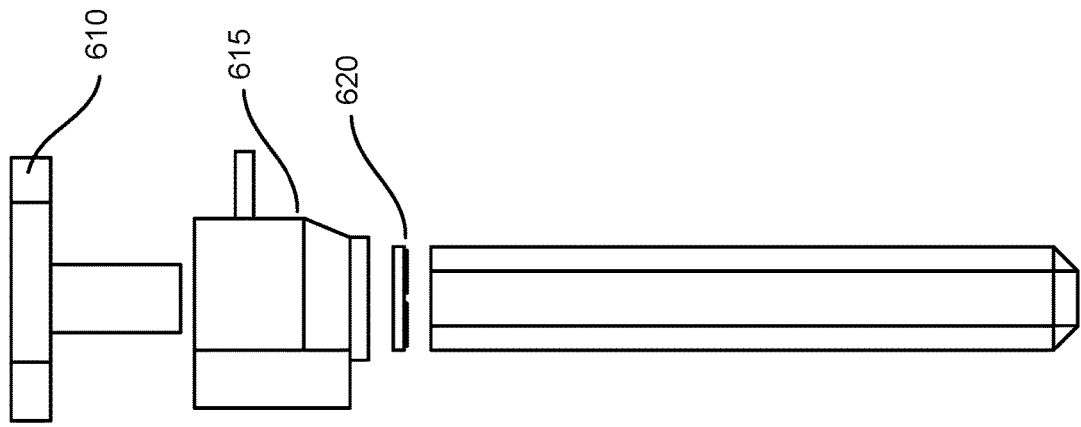
FIG. 6 shows an exploded view of the trocar tool of FIG. 5.
Figure 5:
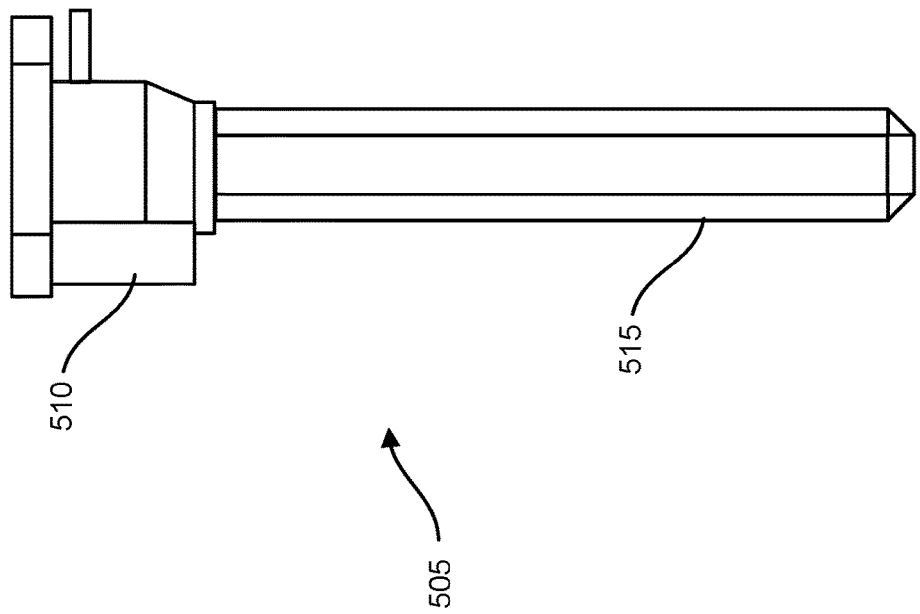
FIG. 5 shows a side view of a trocar tool for use in laparoscopic surgery.

There are now described trocar embodiments of laparoscopic tools. FIG. 5 shows an embodiment of a trocar 505 that includes a proximal hub 510 and a cannula 515 that extends outwardly in a distal direction from the hub 510. FIG. 6 shows an exploded view of the trocar 505. The hub 510 is formed of a proximal-most cap 610, a coupler 615, and a printed circuit board (PCB) 620 positioned at the coupler 615 or between the coupler 615 and the shaft 515. The printed circuit board is coupled to a light source and/or a camera. The hub 510, coupler 615, and PCB 620 collectively couple to the shaft 515 in the assembled state shown in FIG. 5.

Figure 10:
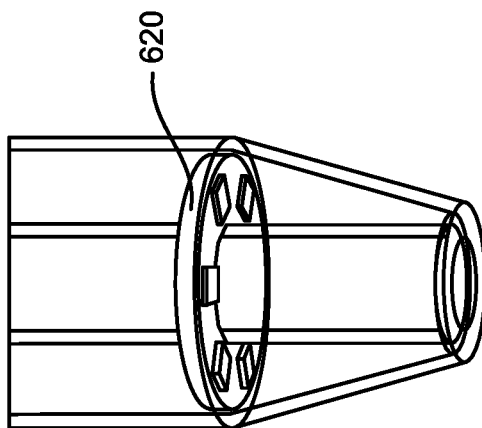
FIGS. 8-10 show enlarged views of portions of the trocar tool.
Figure 9:
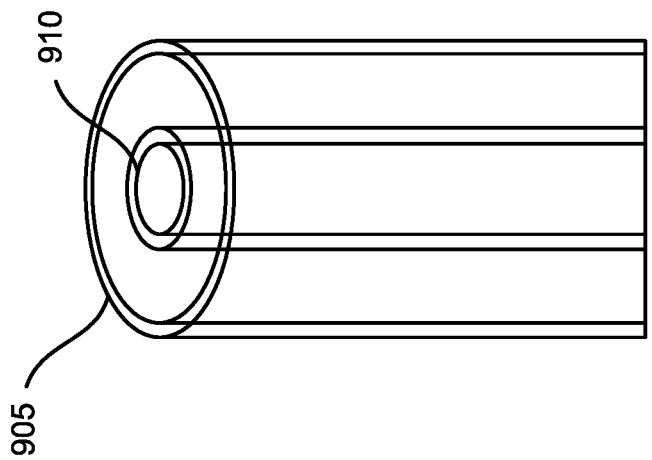
Figure 8:
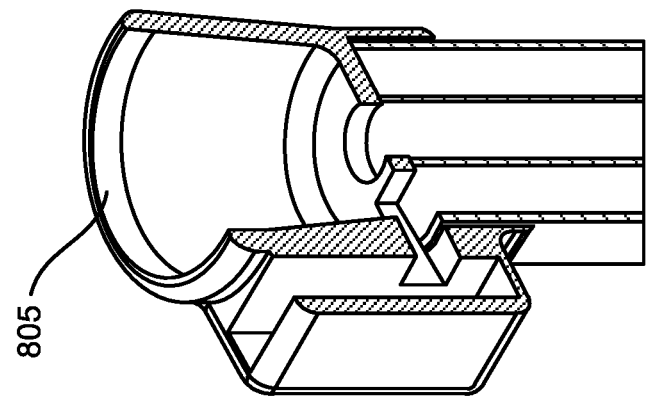

FIG. 7 shows another embodiment of the trocar 705 wherein the printed circuit board and associated electronics (such as a camera and/or a light source) are located near the bottom or distal end (or distal region) of the shaft 515. The shaft 515 is an elongated cylindrical or tubular body that is hollow. It can be manufactured in a variety of manners including via 3-D printing and/or through an injection mold. FIGS. 8-10 show enlarged views of portions of the trocar 705. As shown in FIG. 8, the hub 805 of the trocar defines a cavity that communicates with an internal lumen of the shaft 515. FIG. 9 shows the elongated shaft 515 of the trocar, wherein the elongated shaft is formed of an outer cylindrical body 905 and a central cylindrical body 910 coaxially aligned with the outer cylindrical body 95. As shown in FIG. 10, the distal end of the shaft has a tapered shape with the printed circuit board 620 positioned at or near the distal and at the beginning of the taper (moving in a distal direction).

Figure 11:
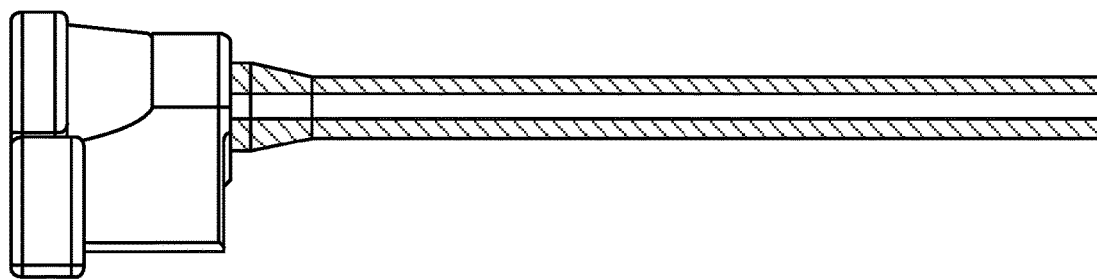
FIG. 11 shows another embodiment of a trocar tool.
Figure 13:
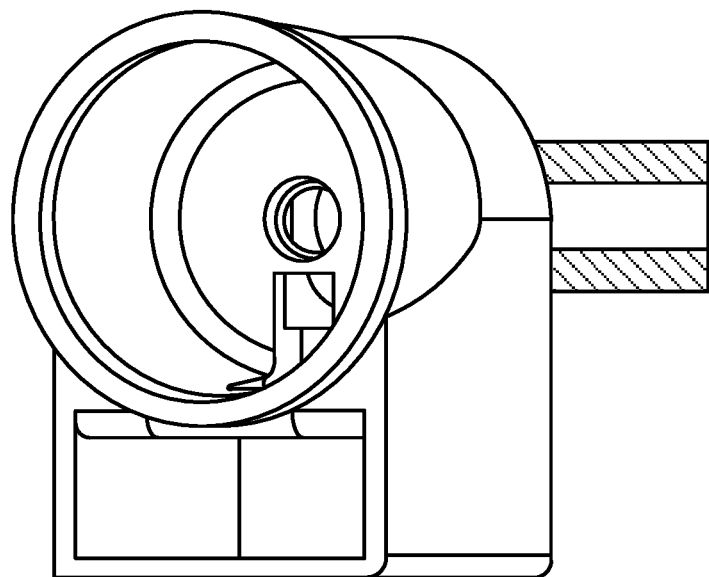
FIGS. 12-13 show enlarged views of portions of the trocar tool.
Figure 12:
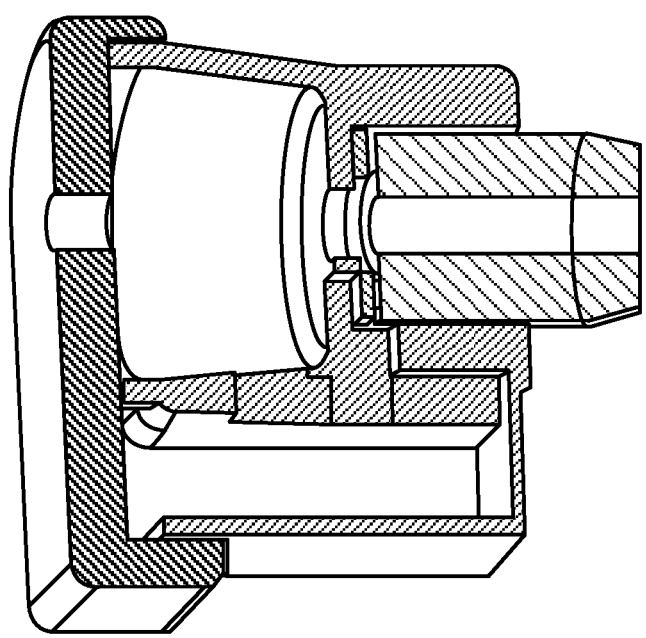

FIG. 11 shows another embodiment of a trocar 1105. In this embodiment, the printed circuit board and associated electronics are positioned at or near the proximal end, or top, of the trocar 1105. The hub can have a large size to accommodate batteries of various sizes, which are positioned inside the hub. FIGS. 12 and 13 show enlarged views of the hub of the trocar 1105. As in previous embodiments, the hub has an internal cavity that communicates with a lumen of the cannula. The hub can also have a removable cap that covers the cavity.

As mentioned, any of the devices described herein can include one or more light sources and/or one or more cameras for obtaining and/or recording images. The devices can also include a built-in power source such as a DC power source including a batter or rechargeable battery. The obtained images can be transmitted wirelessly via a wireless transmitter of the device to a storage device or they can be stored in memory local to the device. In this regard, any of the devices can include a wired or wireless transmitter. Any of a variety of camera types can be used. Any of a variety of wireless capabilities may be provided for transmitting data. For example, the device can transmit data via infrared, radio, Wi-Fi, Bluetooth, etc.

Figure 14:
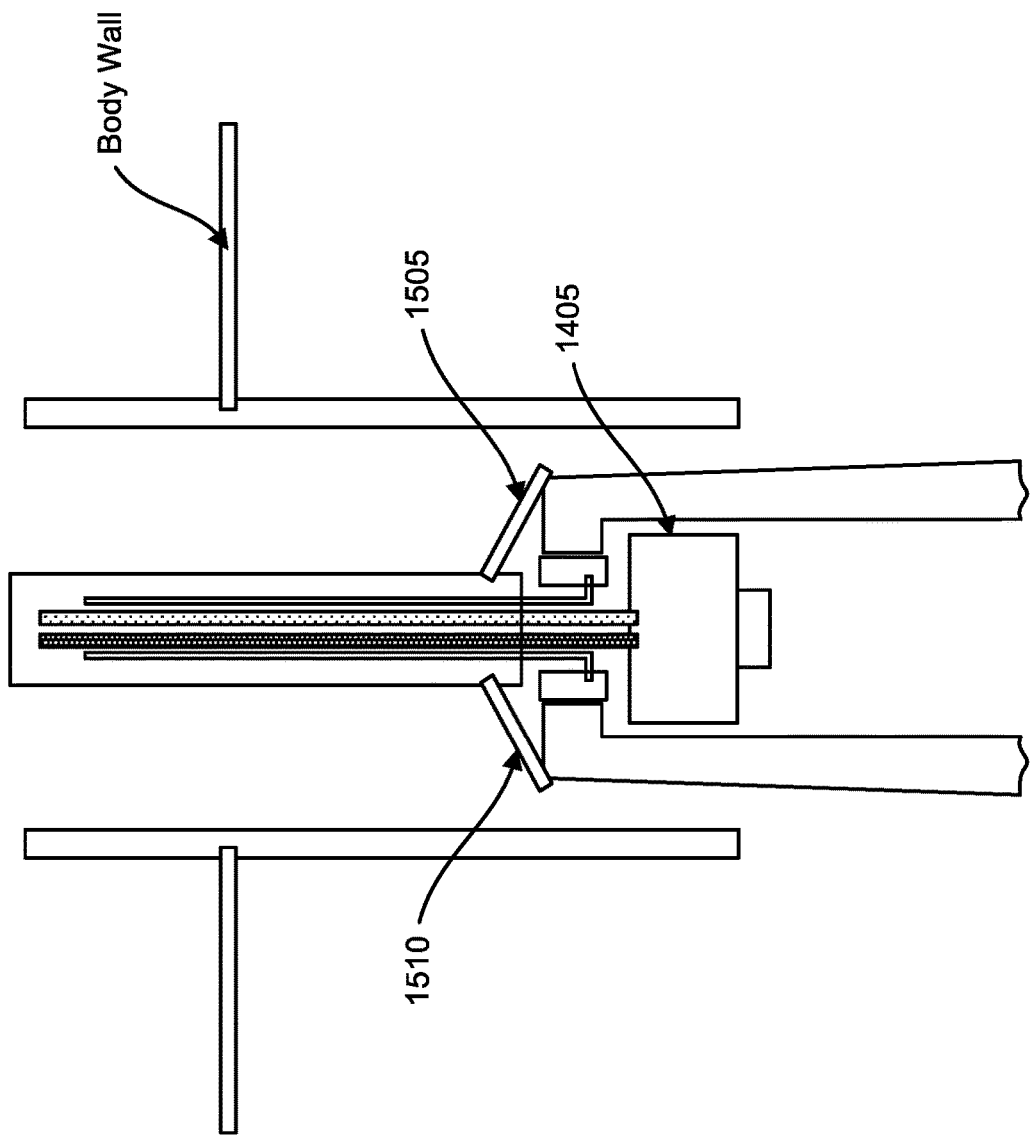
FIGS. 14-16 show schematic representations of camera systems for use in a laparoscopic surgical system.
Figure 15:
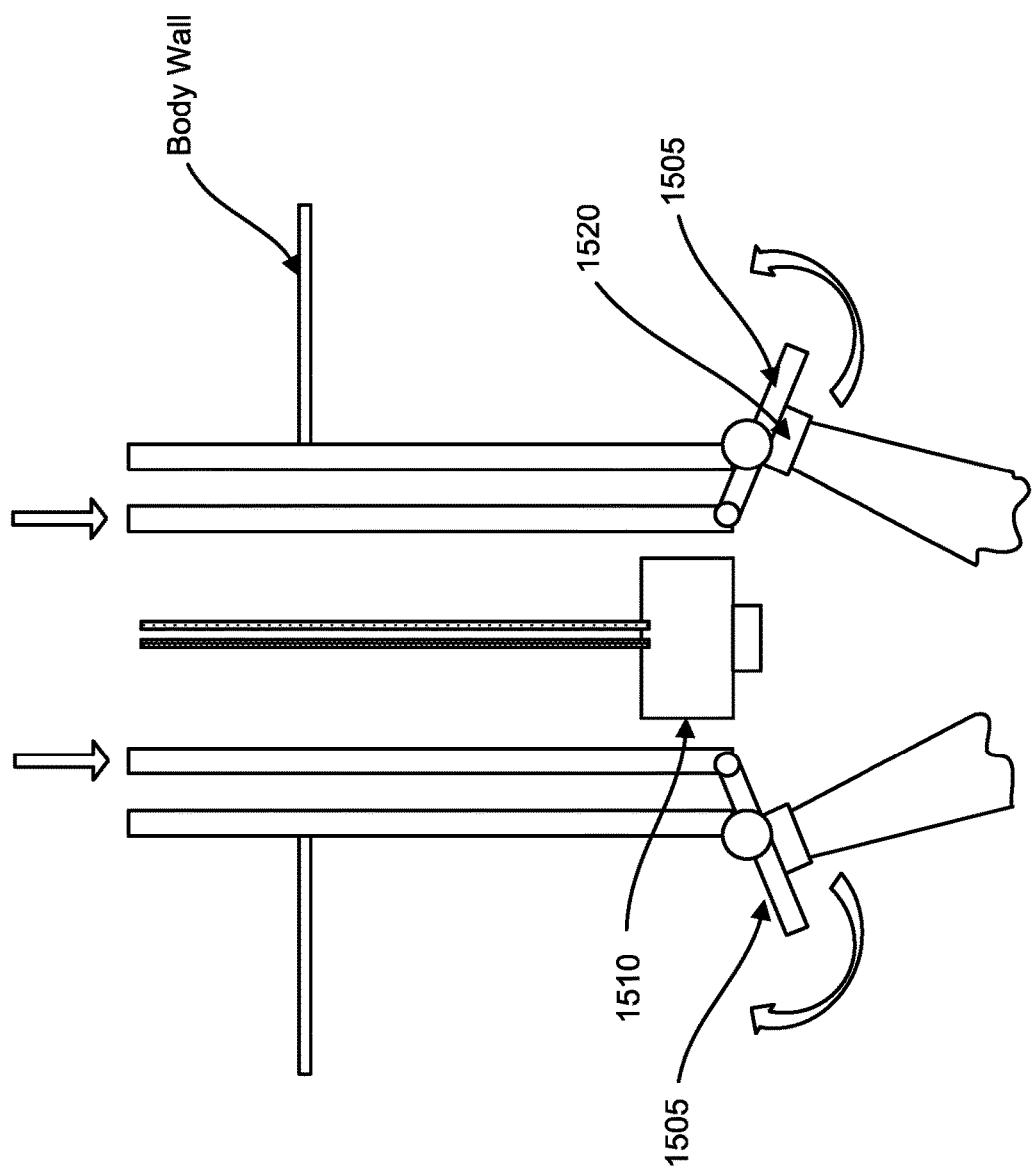
Figure 16:
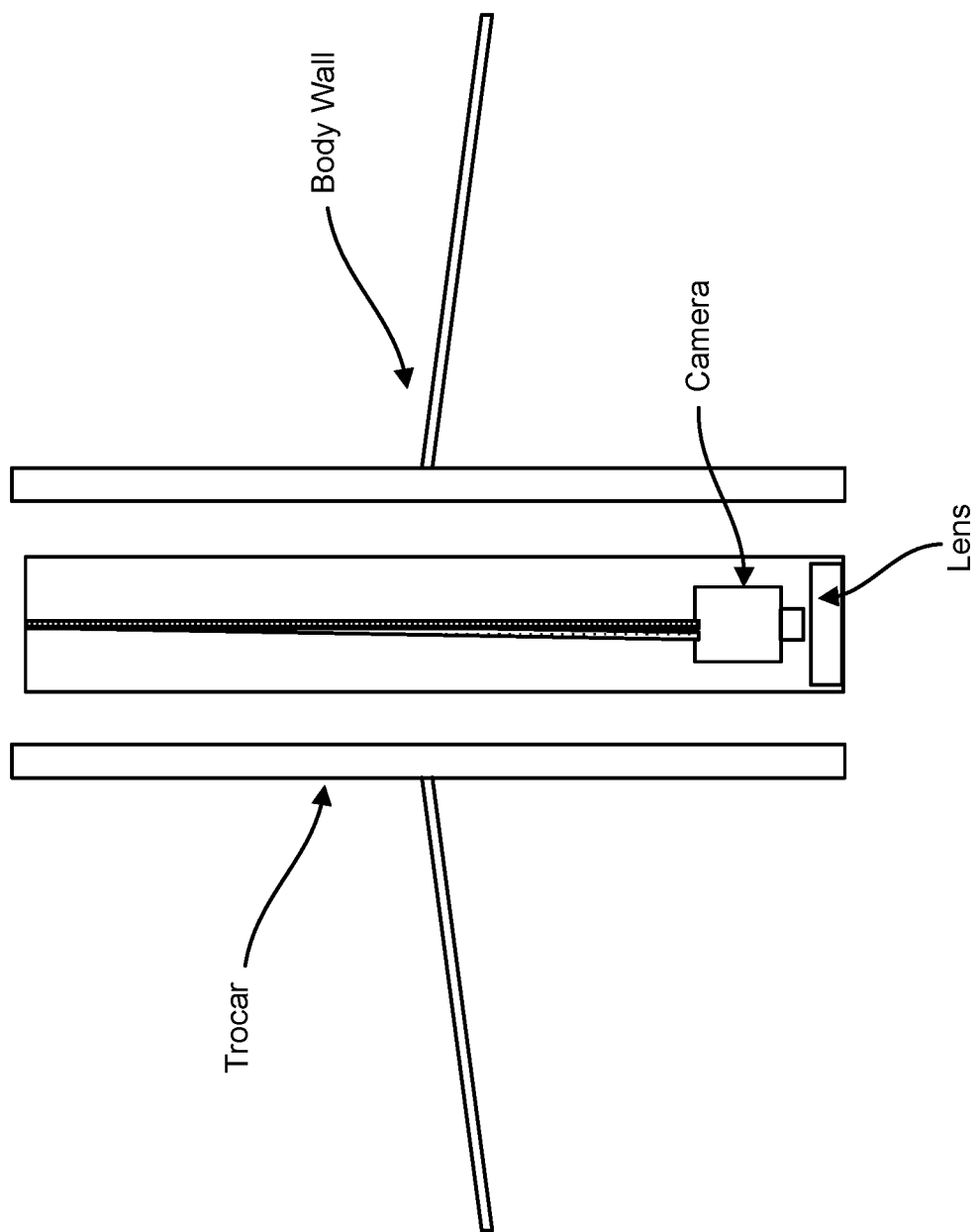

FIGS. 14-16 shows schematic representations of example camera configurations that can be used as part of this devices described herein. With reference to FIG. 14, a mirrored camera configuration is shown and described. A camera 1405 is positioned at a distal end of the device and is positioned distal of a pair of mirrors 1505. The mirrors can be oriented at an angle relative to a ling axis of the device such that the mirrors are not parallel or normal to the long axis. A light source 1510, such as one or more LEDs, is positioned adjacent the camera and distal of the mirrors. When illuminated, the light source 1510 generates light which reflects off of the mirrors in a distal direction. FIG. 14 schematically shows the outer wall (or body wall) of a patient wherein the body wall represents skin of the patient.

FIG. 15 shows another embodiment wherein the mirrors 1505 are hingedly or pivotably attached to the device such that the mirrors 1505 can rotate relative to the device. This permits the mirrors to be rotated to a position such that the mirrors reflect light from the light source 1520 can be aimed at a desired location by an operator. Alternately, the light source(s) 1520 can be mounted on the mirrors and the mirrors rotated to an orientation such that the light is emitted in a direction that corresponds to one or more axes of light transmission.

FIG. 16 shows another embodiment, wherein a single camera is positioned adjacent to (such as proximal of) a lens. The camera is mounted at or near a distal end of the trocar such that the camera can take an image along a direction parallel to a long axis of the trocar. The lens is positioned such that it can adjust the image obtained by the camera. The lens can be removable such that one or more desired lenses can be swamped out.

Figure 17:
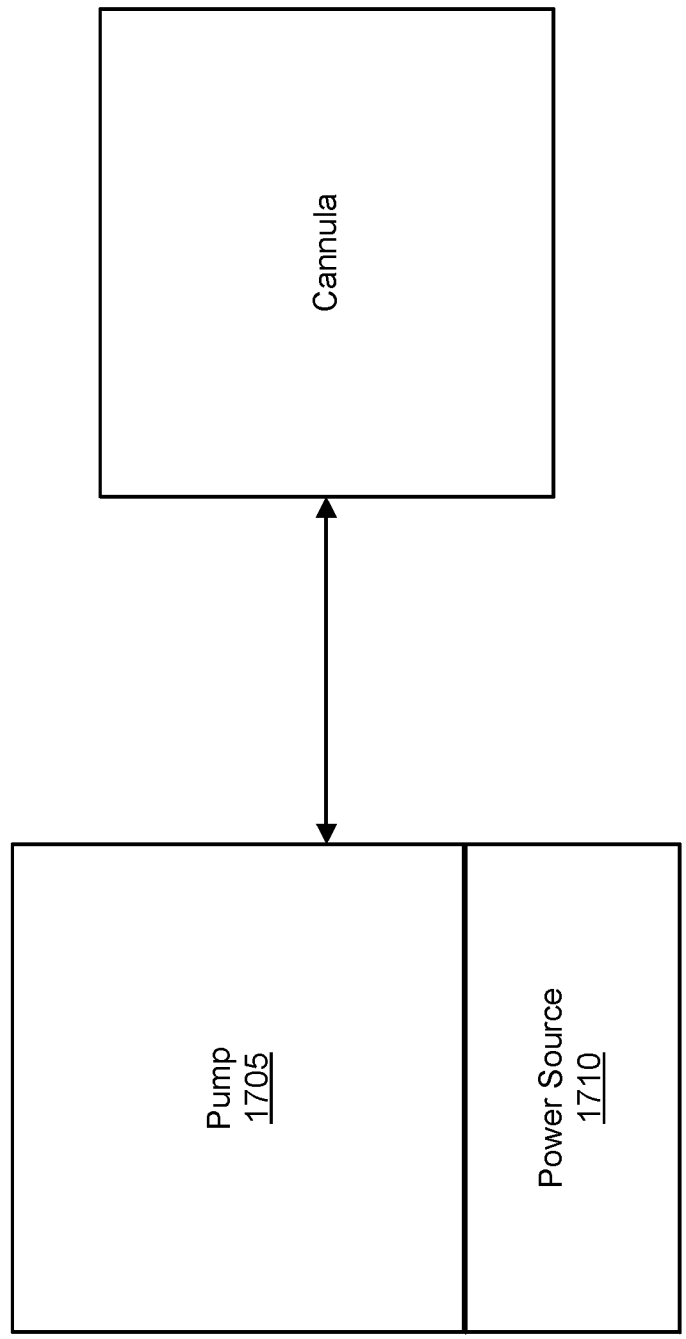
FIG. 17 shows a schematic representation of a smoke evacuator system.
Figure 18:
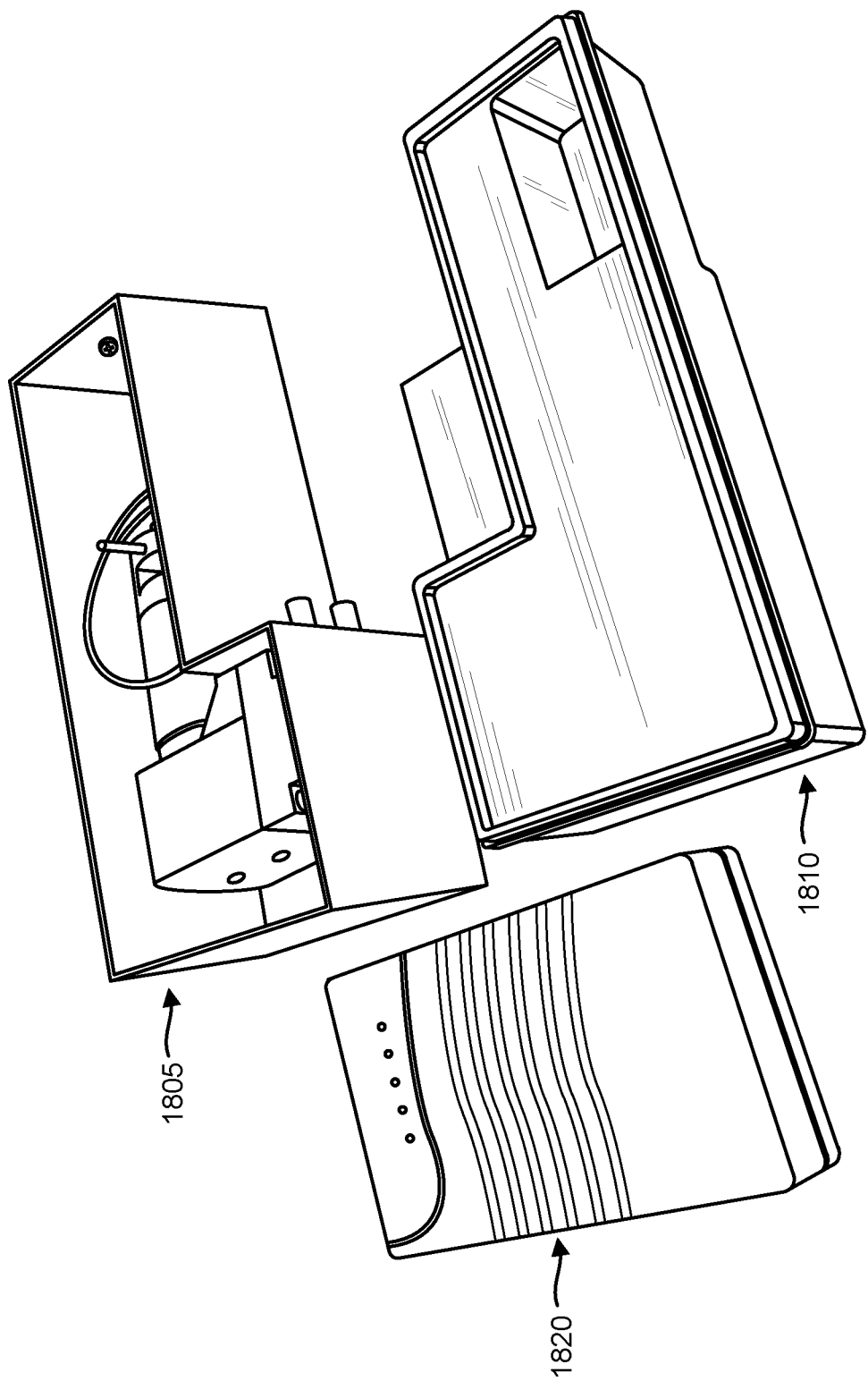
FIGS. 18 and 19 show an example embodiment of the smoke evacuator system.
Figure 19:
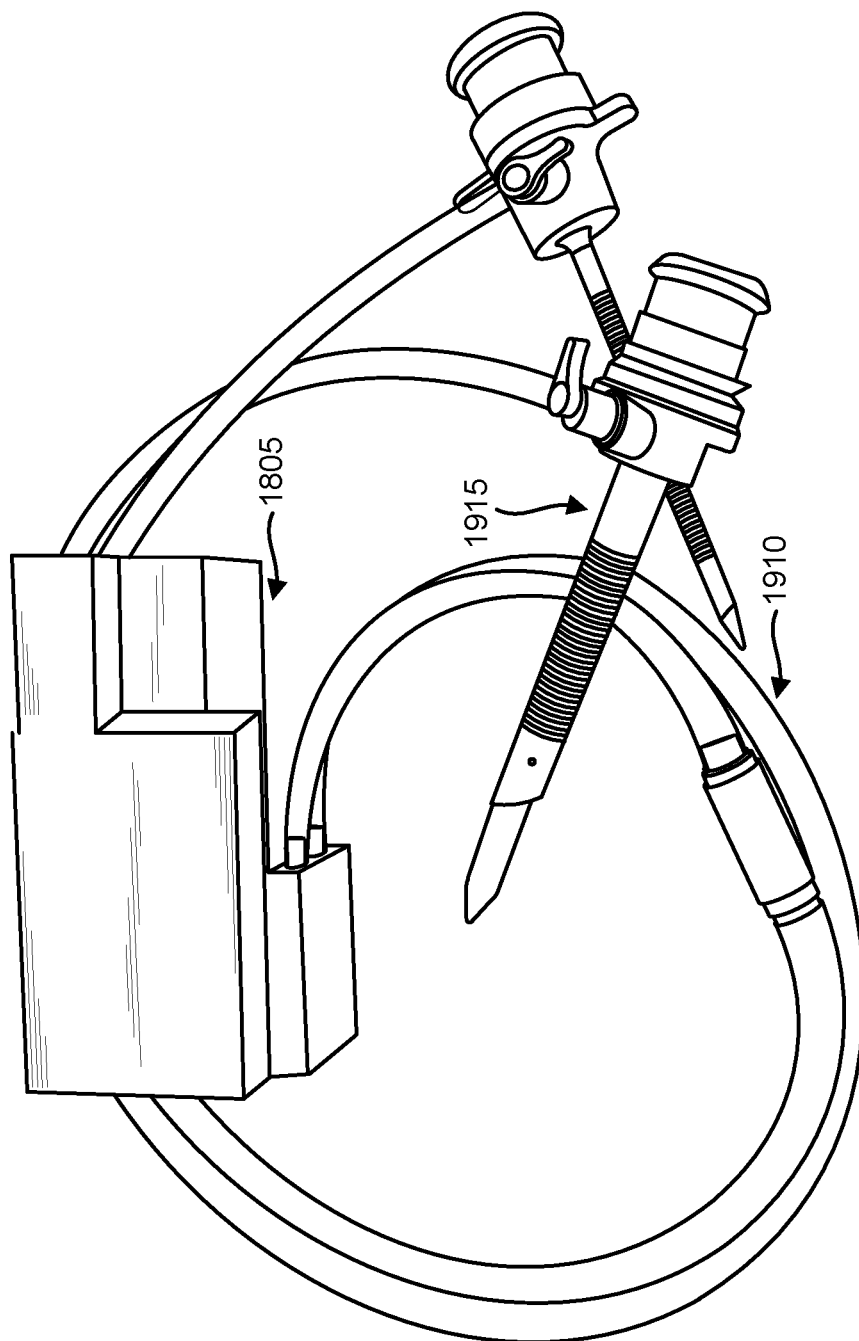

FIGS. 17, 18 and 19 show an embodiment of a smoke evacuator system that can be used as part of the procedure. Smoke generated during surgical procedures has long been thought to be hazardous to hospital personnel. The dangers of surgical smoke are related to the composition of the plume generated during surgery. Small particulate matter are found in the smoke that are easily inhaled. They deposit in the lungs, circulatory system, and other organs which cause numerous detrimental health problems. The smoke also contains many gaseous compounds known to cause cancer. The type of tissue and the form of cautery have been shown to alter the composition of the surgical smoke. Daily inhaled surgical smoke could be equivalent to smoking dozens of cigarettes. Cancer causing compounds have also been found in unsafe levels in the smoke.

FIG. 17 shows a schematic representation of the smoke evacuator system for use during a surgical procedure, such as a laparoscopic surgical procedure. The system includes a pump 1705 coupled to a power source 1710. The pump 7105 is coupled to the light stick, cannula or any other component described herein. The pump is configured to create a pressure differential such that the light stick or canula sucks smoke and/or air into an internal lumen. In this manner, the smoke evacuator system removes smoke created during the procedure such as during cauterization. This improved visibility for the surgeon as smoke may otherwise gather and impede visibility in the absence of the smoke evacuator system. The smoke evacuator system also protects other people in the operating room from potentially biohazardous smoke.

With reference to FIGS. 18 and 19, the smoke evacuator system includes an outer housing or casing 1805 with a removable lid 1810. The casing 1805 defines an internal cavity that may house a power source, such as a chargeable battery, for powering the pump battery system 1820. The casing can also contain a pump 1825, such as a diaphragm pump (in a non-limiting example.)

FIG. 19 shows the casing/pump coupled to one or more hoses or tubes 1910 through which a pressure differential may be formed by the pump for pumping fluid into and through the tubes. The tube(s) 1910 can have a distal end that is positioned at a surgical site for drawing smoke from the surgical site into the tube as a result of a pressure differential caused by the pump. The casing can have intake and outtake ports through which fluid can flow. In addition, the smoke evacuator system can be integrated or otherwise coupled to the trocars/light sticks described herein. In this regard, the tube(s) 1910 can fluidly communicate with internal lumen(s) of a trocar 1915 or light stick (such as those described herein) such as via a respective hub of the trocar/light stick. The smoke evacuator system can also include a filter for filtering air. The filter can be, for example, a HEPA and activated charcoal filter. In a method of use, a person uses a trocar, light stick, cannula (such as the type described herein) pursuant to a laparoscopic surgical procedure. The person can activate the pump to suck or otherwise draw smoke out of the surgical field or general environment via the pump.

Figure 20:
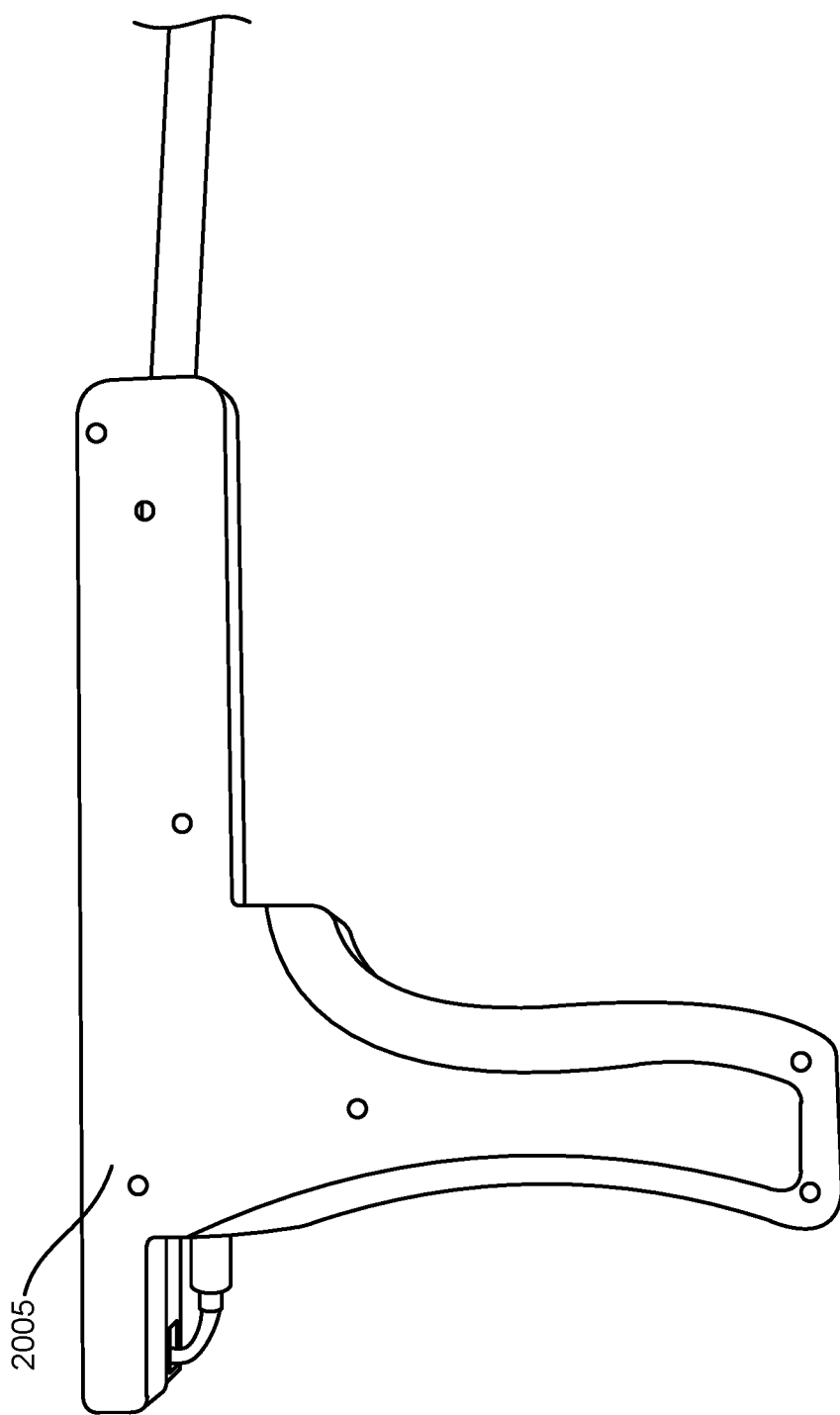
FIG. 20 shows an example of a camera component that can be used with the procedure.

FIG. 20 show an example of a camera component that can be used with the procedure. The camera component be integrated or otherwise coupled to the trocars/light sticks described herein so as to provide real-time and clear images of the surgical area. The camera can be mechanically or wirelessly coupled to a viewing platform, such as a monitor, for displaying the images. As shown in FIG. 20, the camera component can be contained within a pistol-shaped body 2005 that has an ergonomic handle configured to be grasped by a user. The camera can be, for example, a pancellent boroscope camera that wirelessly transmits images. The camera can be wirelessly paired with other devices, such as a monitor, mobile phone, tablet, or other device. The camera may provide a first-person view of the surgical site pursuant to use of the camera during a laparoscopic surgical procedure.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Although embodiments of various methods and devices are described herein in detail with reference to certain versions, it should be appreciated that other versions, embodiments, methods of use, and combinations thereof are also possible. Therefore, the spirit and scope of the appended claims should not be limited to the description of the embodiments contained herein.

The invention claimed is:
1. A system for evacuating smoke in a surgical setting, comprising:
 a smoke evacuation component including:
  a housing;
  a pump contained in the housing;
  a power source coupled to the housing;
  a tube coupled to the pump, wherein the tube has a portion positionable at a surgical site for drawing smoke from the surgical site as a result of a pressure differential caused by the pump; and
 a laparoscopic surgical device including:
  a hub attached to the tube of the smoke evacuation component;
  a cannula extending outwardly from the hub
  a camera is positioned at a distal region of the cannula;
  a plurality of mirrors positioned at the distal region of the cannula;
  a light source positioned adjacent the camera and the plurality of mirrors such that, when illuminated, the light source generates light that reflects off of the mirrors in a distal direction.

2. The system of claim 1, wherein the power source is a battery.

3. The system of claim 2, wherein the batter is contained inside the housing.

4. The system of claim 1, wherein the battery is rechargeable.

5. The system of claim 1, wherein the tube can be coupled to a laparoscopic surgical device.

6. The system of claim 1, wherein the light source comprises at least one light emitting diode.

7. The system of claim 1, wherein the camera is positioned distal of the plurality of mirrors.

8. The system of claim 1, wherein the plurality of mirrors is oriented at an angle relative to a long axis of the cannula such that the mirrors are not parallel or normal to the long axis.

9. The system of claim 1, wherein the plurality of mirrors is pivotably attached to the cannula such that the plurality of mirrors can rotate relative to the cannula.

10. The system of claim 9, wherein the light source is mounted on the plurality of mirrors such that the light source rotates to an orientation via rotation of the plurality of mirrors.

* * * * *